(12) United States Patent
Heuer et al.

(10) Patent No.: US 7,772,428 B2
(45) Date of Patent: Aug. 10, 2010

(54) CREATINE HYDROXYCITRIC ACIDS SALTS AND METHODS FOR THEIR PRODUCTION AND USE IN INDIVIDUALS

(75) Inventors: Marvin Heuer, Oakville (CA); Michele Molino, Oakville (CA)

(73) Assignee: Northern Innovations and Formulations, Oakville, ON (CA)

( * ) Notice: Subject to any disclaimer, the term of this patent is extended or adjusted under 35 U.S.C. 154(b) by 0 days.

(21) Appl. No.: 12/108,822

(22) Filed: Apr. 24, 2008

(65) Prior Publication Data

US 2008/0300309 A1 Dec. 4, 2008

Related U.S. Application Data

(62) Division of application No. 11/349,960, filed on Feb. 7, 2006, now abandoned.

(60) Provisional application No. 60/651,049, filed on Feb. 7, 2005.

(51) Int. Cl.
C07C 229/00 (2006.01)
C07C 391/00 (2006.01)

(52) U.S. Cl. .................. 562/561; 562/560; 562/568

(58) Field of Classification Search .................. None
See application file for complete search history.

(56) References Cited

U.S. PATENT DOCUMENTS

| 5,925,278 | A | 7/1999 | Hirst |
| 5,973,199 | A | 10/1999 | Negrisoli et al. |
| 6,166,249 | A | 12/2000 | Pischel et al. |
| 6,211,407 | B1 * | 4/2001 | Thomson ............... 562/560 |
| 6,838,562 | B2 | 1/2005 | Abraham et al. |
| 2004/0185069 | A1 * | 9/2004 | Gupta ................... 424/401 |
| 2006/0280814 | A1 * | 12/2006 | Gardiner et al. ......... 424/729 |
| 2008/0089962 | A1 * | 4/2008 | Heuer ................... 424/775 |
| 2009/0155379 | A1 * | 6/2009 | Heuer ................... 424/602 |

OTHER PUBLICATIONS

Persky et al. Clinical pharmacology of the dietary supplement creatine monohydrate. Pharmacol Rev. 53(2);161-76, 2001.
Harris et al. Elevation of creatine in resting and exercised musce of normal subjects by creatine supplementation. Clincal Science. 83:367-74, 1992.
Balson et al. Skeletal muscle metabolism during short duration high intensity exercise: influence of creatine supplementation. Acta Physiologica Scandinavica. 1154:303-310, 2995.
Jena et al. Chemistry and Biochemistry of (-)Hydroxycitric acid from garcinia. J Agric Food Chem. 50:10-20, 2002.
Preuss et al. Efficacy of a novel, natural extract of (-) hydroxycitric acid (HCA-SX) and a combination of HCA-SX, niacin-bound chromium, and Gymnema sylvestre extract in weight management in human volunteers: a pilot study. Nutrition Research. 24:45-58, 2004.
PCT/CA/2006/000159. International Search Report. Date of issuance of this report Mar. 15, 2006.
Sullivan et al., Effect of (-)-Hydroxycitrate upon the Accumulation of Lipid in the Rat: II. Appetite; Lipids, vol. 9, No. 2, (1973) pp. 129-134.

* cited by examiner

Primary Examiner—Karl J Puttlitz

(57) ABSTRACT

Methods of production for Tricreatine Hydroxycitrate are disclosed. Tricreatine hydroxycitrate can be used as supplemental dietary ingredient for the purposes of reducing adiposity, suppression of appetite, improvement of muscle and exercise performance and recovery. The salts are useful in the dietetic, food supplement and food industries.

20 Claims, No Drawings

CREATINE HYDROXYCITRIC ACIDS SALTS AND METHODS FOR THEIR PRODUCTION AND USE IN INDIVIDUALS

RELATED APPLICATIONS

This application is a divisional of and claims the benefit of priority from U.S. patent application Ser. No. 11/349,960, filed on Feb. 7, 2006, now abandoned which in turn is related to and claims benefit of priority from U.S. Provisional Patent Application Ser. No. 60/651,049, entitled "Creatine Hydroxycitric Acids Salts and Methods for their Production and Use in Individuals," filed Feb. 7, 2005, the disclosures of which are hereby fully incorporated by reference.

FIELD OF THE INVENTION

The present invention relates to a supplemental dietary ingredient that promotes increased muscle and exercise performance in individual, reduces and/or prevents adiposity, improves exercise recovery, and/or suppresses the appetite leading to weight loss. The present invention is also related to a method of promoting same by consuming the supplemental composition. The invention also relates to a method for producing a supplemental composition.

BACKGROUND

Creatine monohydrate is a commonly used supplement. Creatine monohydrate is soluble in water at a rate of 75 ml of water per gram of creatine. Ingestion of creatine monohydrate thereof requires large amounts of water to also be ingested. Additionally, in aqueous solutions, creatine converts to creatinine via an irreversible, pH-dependent, non-enzymatic reaction. Aqueous and alkaline solutions contain an equilibrium mixture of creatine and creatinine. In acidic solutions, on the other hand, the formation of creatinine is complete. Creatinine is devoid of the ergogenic beneficial effects of creatine.

Hydrosoluble creatine monohydrate salts are obtainable and have been described elsewhere. For instance, U.S. Pat. No. 5,973,199, incorporated herein in its entirety by reference, purports to describe hydrosoluble organic salts of creatine as single combination of one mole of creatine monohydrate with one mole of the following organic acids: citrate, malate, fumarate, tartarate, and malate.

U.S. Pat. No. 5,925,278, incorporated herein in its entirety by reference, purports to describe a form of a creatine salt as a combination of one mole of creatine with one mole of citric acid.

U.S. Pat. No. 6,211,407, incorporated herein in its entirety by reference, purports to describe dicreatine and tricreatine citrate and methods of making the same. Salts are reported to be a combination of two and three moles of creatine monohydrate with one mole of citric acid, respectively. In addition, dicreatine and tricreatine citrate are claimed to be stable in acidic solution, in a guise to prevent or impede the formulation of creatine to creatinine.

U.S. Pat. No. 6,166,249, incorporated herein in its entirety by reference, purports to describe a creatine pyruvic acid salt where the ratio of creatine to pyruvate is 1:1 and the creatine pyruvate contains 1-10 molecules of water.

U.S. Pat. No. 5,973,199, incorporated herein in its entirety by reference, purports to describe a method of producing a creatine malate salt with a melting point of between 128 and 129° C. The patent also purports to describe a method of producing a creatine citrate salt with a melting point between 112 and 114° C.

U.S. Pat. No. 6,838,562, incorporated herein in its entirety by reference, purports to describe a process for the synthesis of mono, di, or tricreatine orotic acid, thioorotic acid, and dihydroorotic acid salts.

SUMMARY OF THE INVENTION

The present invention, according to various embodiments thereof, provides methods for the production the and use in individuals, e.g. animals and human, of organic salts formed via the reaction of creatine (as used herein, this term shall refer to any type of creatine and shall not be limited to any particular form or anion) with hydroxycitric acid (also referred to "HCA"), the principle acid occurring in the rind of fruits from plants of the *Garcinia* genus (including, but not limited to, *Garcinia cambogia, Garcinia indica*, and *Garcinia atrovirids*). These salts, e.g. monocreatine hydroxycitrate, dicreatine hydroxycitrate, and tricreatine hydroxycitrate (collectively referred to as "creatine hydroxycitrates"), may provide improved hydrosolubility and possess ameliorated stability in water and in acidic solutions compared to creatine monohydrate. The aforementioned creatine hydroxycitrates may be useful to increase muscle and exercise performance in individuals, athletes in particular, and to afford neuroprotective strategies addressing specific bioenergetic defects. In addition, by supplying biosignificant amounts of HCA, these creatine hydroxycitrates may contribute to reduce fatty acid synthesis by preventing the conversion of carbohydrate energy into triglycerides, thereby being particularly suitable to be used in conjunction with dietary and exercise regimens aimed at the reduction and/or prevention of excess adiposity leading to weight loss. Furthermore, the creatine hydroxycitrates, due to a stimulatory action of the HCA moiety on serotonergic output, may contribute to improved exercise recovery and suppress the appetite leading to weight loss.

Generally, the present invention, according to various embodiments thereof, provides stable hydrosoluble creatine hydroxycitric acid salts, e.g. creatine hydroxycitrates, and a method of producing same, that possess higher water solubility and stability in acidic solutions compared to creatine monohydrate. The present invention, according to various embodiments thereof, may also provide creatine hydroxycitrates, and a method of producing the same, that may be administered orally to a mammal with a bioavailability equal to or higher than creatine or hydroxycitric acid administered singularly or as a combination, wherein the salts may synergistically increase the physiological benefits afford by the single creatine and the hydroxycitric acid components.

More specifically, the present invention provides a method of production for a supplemental dietary ingredient, and a method of producing the same, that provides bioavailable organic creatine salts, e.g., monocreatine, dicreatine, and tricreatine hydroxycitrate, also collectively describable as "creatine hydroxycitrates". Advantageously, the present invention provided for a supplemental dietary ingredient and a method of producing the same, in which the bioavailable organic creatine salts include one, two or three energy-enhancing cationic portions (represented by creatine, which as set forth above is not limited to any particular type or anion) per lipolytic/anti-lipogenic anionic portion (represented by hydroxycitrate), respectively. Also, the present invention may, according to one embodiment, provide creatine hydroxycitrates, and a method of producing the same, which possess ameliorated palatability.

The present invention also provides by the consumption of a supplemental composition containing creatine hydroxycitric acid, a method of promoting increased muscle and exercise performance in individuals. The present invention may also provide, by the consumption of a supplemental composition containing a creatine hydroxycitric acid or derivative, a method of reducing and/or preventing adiposity. The present invention may also provide, by the consumption of the supplemental composition a containing creatine hydroxycitric acid or derivative, a method of improving exercise recovery. In addition, the present invention may also provide, by the consumption of a supplemental composition containing a creatine hydroxycitric acid or derivative a method suppressing appetite leading to weight loss.

Supplementation with creatine hydroxycitrate, according to various embodiments of the present invention, may be utilized by individuals engaged in sports where a need exists to improve short-term anaerobic performance and/or achieve simultaneous muscle volumization and leanness. Moreover, due to HCA-induced stimulation of serotonergic output resulting from supplementation with creatine hydroxycitrates, recovery from exercise and minimize feeding urges (especially during strict dietary restriction) are ameliorated. Furthermore, creatine hydroxycitrates, by affording Neuroprotection, may be particularly useful in addressing specific bioenergetic defects in Huntington's and Parkinson's diseases, Duchene muscular dystrophy, and may be utilized clinically in patients with gyrate atrophy, and other various neuromuscular disorders, McArdle's disease, and congestive heart failure.

In one embodiment, the present invention is directed towards isolated hydrosoluble salts of creatine formed via the reaction of creatine with hydroxycitric acids, e.g., creatine hydroxycitrates, the salts having ameliorated stability in water and acidic solutions compared to creatine monohydrate.

In one embodiment, the creatine hydroxycitrates are monocreatine, dicreatine, and tricreatine hydroxycitrate. The monocreatine hydroxycitrate may include one creatine cation per hydroxycitrate anion. The dicreatine hydroxycitrate may include two creatine cations per hydroxycitrate dianion. The tricreatine hydroxycitrate may include three creatine cations per hydroxycitrate trianion.

The present invention may provide a method for enhancing muscle performance and exercise recovery and weight loss in individuals, e.g., athletes, wherein the method comprises administering a composition comprising any of the isolated salts described herein, singularly and in combination. The present invention may also provide a method for affording neuroprotective strategies addressing specific bioenergetic defects, the method including administering a composition comprising any of the isolated salts described herein, singularly and in combination. The present invention may also provide a method for affording recovery from fatigue and stress wherein the method includes administering a composition comprising any of the isolated salts described herein, singularly and in combination. The present invention may also provided a method for reducing fatty acid synthesis by preventing the conversion of carbohydrate energy into triglycerides wherein the method includes administering a composition comprising any of the isolated salts described herein, singularly and in combination. Also, the present invention may provide a method for suppressing appetite leading to weight loss by stimulating serotonergic output wherein the method comprises administering a composition comprising any of the isolated salts described herein, singularly and in combination.

The present invention may also provide a method which advantageously includes the steps of combing with any of the isolated salts described herein with one or more of the following dietary ingredients: Whey protein (isolates and/or concentrates and/hydrolysates), casein (micellar casein, sodium and/or calcium caseinates), alpha lipoic acid, carbohydrates, free-form amino acids (branched-chain and/or essential and/or non-essential amino acids) and salts, trivalent chromium and its organic salts and chelates (chromium polynicotinate and/or picolinate, and/or fumarate, citrate, etc.), vitamins and minerals, *camellia sinensis* leaf and its polyphenolic extracts (containing in particular: epigallocatechin gallate (EGCG), epigallocatechin (EGC), catechin (C), epicatechin (EC), epicatechin gallate (EG), etc.), caffeine and other thermogenics, bioflavonoids, condensed tannins, oligomeric proanthocyanidins, American and/or Korean ginseng and their extracts (containing in particular ginsenoside-type glycosidal saponins), konjac glucomannan, creatinol including derivatives of creatinol such as ester, amides, and salts as well as other derivatives, including derivative that become active upon metabolism, and creatinol O-phosphate (COP), creatinol sulfate (CS), policosanol, adaptogenic herbs and remedies, etc. It should be recognized that the ingredients which may be added to or in conjunction with the dietary salts in accordance with present invention are not limited to the ingredients listed above.

In accordance with an embodiment, the present invention relates to an isolated hydrosoluble salt of creatine and hydroxycitrate of the formula:

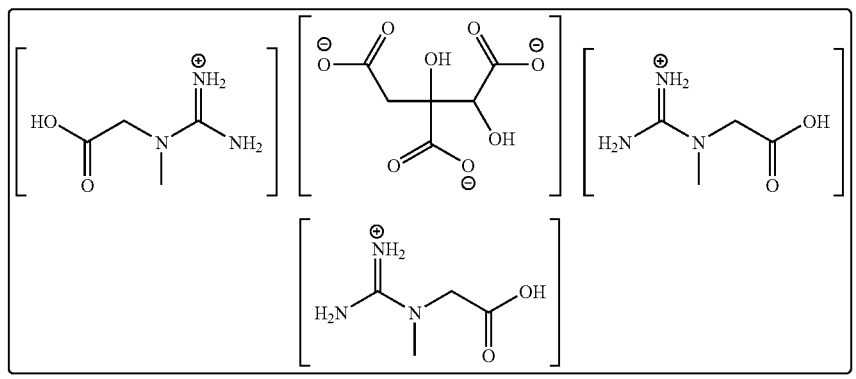

The hydrozoluble salt may have a molecular weight of 599.55, and a melting point of about 290° C.

In addition, in accordance with an embodiment, the present invention relates to a method for at least one of promoting increased muscle and exercise performance in individuals, reducing and/or preventing adiposity, improving exercise recovery and suppressing the appetite of an individual leading to weight loss, the method including the step of consuming a supplemental dietary composition containing creatine hydroxycitric acid in the form of an isolated hydrosoluble salt of creatine and hydroxycitrate. The hydrosoluble salt may have a molecular weight of 599.55, and a melting point of about 290° C.

In accordance with an embodiment, the present invention relates to a supplemental dietary composition for at least one of promoting increased muscle and exercise performance in individuals, reducing and/or preventing adiposity, improving exercise recovery and suppressing the appetite of an individual leading to weight loss, the supplemental dietary composition including creatine hydroxycitric acid in the form of an isolated hydrosoluble salt of creatine and hydroxycitrate. In the supplemental dietary composition, the salt may have a molecular weight of 599.55, and a melting point of about 290° C.

DETAILED DESCRIPTION OF THE INVENTION

When supplemented with exogenous creatine, intramuscular and cerebral stores of creatine and its phosphorylated form, phosphocreatine, become elevated. The increase of these stores can offer therapeutic benefits by preventing ATP depletion, stimulating protein synthesis or reducing protein degradation, and stabilizing biological membranes. Evidence from the exercise literature has shown that athletes benefit from creatine supplementation by an increase in muscular force and power, reducing fatigue in repeated bout activities, and increasing muscle mass. During brief intense exercises, e.g., a duration of a ½ minute or less, phosphocreatine is broken down to creatine and phosphate, and the energy release is used to regenerate the primary source of energy, i.e., adenosine triphosphate (ATP). When phosphocreatine becomes depleted, output of power falls because ATP may not be regenerated fast enough to meet the demand of the exercise. Consequently, a larger accumulation of phosphocreatine is muscle is able reduce fatigue during brief intense exercise bouts.

Extra creatine in the muscle may also increase the rate of regeneration of phosphocreatine following high-intensity anaerobic exercise, which may result in less fatigue with repeated bursts of activity in training or in many sport competitions.

Thus, creatine supplementation may result in positive physiologic effects on skeletal muscle, such as: performance improvements during brief high-intensity anaerobic exercise, increased strength and ameliorated body composition in physically active subjects. These benefits have been applied to disease models of Huntington's, Parkinson's, Duchene muscular dystrophy, and utilized clinically in patients with gyrate atrophy, various neuromuscular disorders, McArdle's disease, and congestive heart failure. See, for instance, Persky, A. M., and Brazeau, G. A., "Clinical pharmacology of the dietary supplement creatine monohydrate". *Pharmacol Rev* 53(2):161-176, 2001. Dietary supplementation with synthetic creatine has become increasingly common, representing the primary way athletes "load" the muscle with creatine. Daily doses of about 20 g of creatine for 5-7 days usually increases the total creatine content in the muscle by 10-25%. About one-third of the extra creatine in muscle is in the form of phosphocreatine. See, for instance, Harris, R., et at., "Elevation of creatine in resting and exercised muscle of normal subjects by creatine supplementation". *Clinical Science* 83:367-374, 1992; and Balson, P., et al., "Skeletal muscle metabolism during short duration high0intensity exercise; influence of creatine supplementation". *Acta Physiologica Scandinavica*, 1154:303-310, 2995.

Hydroxycitric acid has been shown to inhibit the activity of ATP citrate lyase, the extramitochondrial enzyme responsible for the conversion of carbohydrate energy into fats, and therefore it is believed to suppress fatty acid synthesis, lipogenesis, and induce weight loss; see, for instance Jena, B. S., et al., "Chemistry and Biochemistry of (−)-Hydroxycitric Acid from Garcinia". *J Agric Food Chem* 50:10-20, 2002. Additional evidence has also been presented to the extent that hydroxycitric acid may reduce food intake by means of a stimulatory action on serotonergic output, which ultimately induces satiety and reduced the urge of the individual feed; see, for instance Preuss, H. G., et al., "Efficacy of a novel, natural extract of (−)-hydroxycitric acid (HCA-SX) and a combination of HCA-SX, niacin-bound chromium, and *Gymnema sylvestre* extract in weight management in human volunteers: A pilot study". *Nutrition Research* 24:45-58, 2004. Supplementation with hydroxycitric is conventionally employed as a dietary intervention to fight obesity and over-weightedness leading to weight loss. Additionally, hydroxycitric acid has found application in sports nutrition to help active individuals and professional athletes to reach and maintain optimum level of body fat that many sports discipline may require.

The present invention according to various embodiments thereof (refer to examples 1 to 4) provides stable hydrosoluble creatine hydroxycitric acids salts, e.g., creatine hydroxycitrates, such as tricreatine hydroxycitrate, and a method for producing the same, that possess higher water solubility and stability in acidic solutions compared to creatine monohydrate. The present invention, according to various embodiments thereof, provides creatine hydroxycitrates, such as tricreatine hydroxycitrate, and a method for producing the same, that may be administered orally to a mammal with a bioavailability equal to or higher than creatine or hydroxycitric acid administered singularly or as a combination, wherein the salts may synergistically increase the physiological benefits afforded by the single creatine and the hydroxycitric acid components.

More specifically, the present invention provide for a supplemental dietary ingredient, and a method for producing the same, that provides bioavailable organic creatine salts, e.g., creatine hydroxycitrates. Advantageously, the present invention provides for a supplemental dietary ingredient and a method for producing the same, in which the bioavailable organic creatine salts include one, two, or three energy-enhancing cationic portions (represented by creatine) per lipolytic/anti-lipogenic anionic portion (represented by hydroxycitrate), respectively. Also, the present invention may provide creatine hydroxycitrates, and a method for producing the same, which possess ameliorated palatability.

The present invention also provides by the consumption of a supplemental dietary composition containing creatine hydroxycitric acid, a method of promoting increased muscle and exercise performance in individuals. The present invention may also provide, by the consumption of a supplemental dietary composition containing creatine hydroxycitric acid, a method of reducing and/or preventing adiposity. The present invention may also provide, by the consumption of a dietary supplemental composition containing creatine hydroxycitric acid, a method of improving exercise recovery. In addition, the present invention may also provide, by the consumption of a supplemental dietary composition containing creatine hydroxycitric acid, a method of suppressing the appetite of an individual, leading to weight loss.

In this regard, supplementation with creatine hydroxycitrates, according to various embodiments of the present invention, may be particularly suitable in sports where a need exists to improve short-term anaerobic performance and/or achieve simultaneous muscle volumization and leanness. Moreover, due to HCA-induced stimulation of serotonergic output, supplementation with creatine hydroxycitrates, according to various embodiments of the present invention, may be particularly suitable to enhance recovery from exercise and minimize feeding urges (especially during strict dietary restriction). Furthermore, creatine hydroxycitrates, by affording Neuroprotection, may be particularly suitable in addressing specific bioenergetic defects in Huntington's and Parkinson's diseases, Duchene muscular dystrophy, and may be utilized clinically in patients with gyrate atrophy, various neuromuscular disorders, McArdle's disease, and congestive heart failure.

The supplemental ingredient, creatine hydroxycitrate may be consumed in any form. For instance, the dosage form of the supplemental composition may be provided as, e.g., a capsule, a tablet, a caplet, a liquid beverage, a powder beverage mix, a dietary gel, or as ready-to-eat bar or drink product. The preferred dosage forms are capsules or powder.

Furthermore, the dosage may be provided in accordance with customary processing techniques for herbal and/or dietary supplements in any of the forms mentioned above. Those of skill in the art will appreciate that a supplemental composition may contain variety of additional active ingredients and excipients.

In several example embodiments of the present invention, which are set forth in greater detail in Examples 1 through 5 below, there are provided as methods of producing creatine hydroxycitric acid, for promoting increased muscle and exercise performance in individuals, reducing and/or preventing adiposity, improving exercise recovery, and/or suppressing the appetite leading to weight loss.

Thus, the present invention, according to various embodiments thereof, provides stable hydrosoluble creatine HCA salts, e.g., creatine hydroxycitrates, which possess higher water solubility and stability in acidic solutions compared to creatine monohydrates. The present invention, according to various embodiments thereof, may also provide creatine hydroxycitrates that may be administered orally to a mammal with a bioavailability equal to or higher than that of creatine or HCA when administered singularly or in combination, wherein the salts may synergistically increase the physiological benefits afforded by the single creatine or the HCA components.

Referring to the alcohols employed in various steps of the example embodiments illustrated below, it should be noted that preferred alcohols include methyl alcohol, ethyl alcohol, propyl alcohol and isopropyl alcohol. Also, ethyl acetate (acetic acid ethyl ester) may be employed. Most preferably, methyl alcohol is employed. Hydroalcoholic solution of (−)-HCA are preferred in order to reduce the conversion of creatine into creatinine during the time necessary for the reaction to be completed. Water (−)-HCA solution could be alternatively used as a media to which creatine monohydrate is added. The reaction however, would yield salts with lower creatine content.

The present invention, according to various embodiments thereof, may provide certain advantages over conventional dietary supplement ingredients and method of producing the same. For instance, the creatine hydroxycitrates of the present invention may have improve hydrosolubility and possess ameliorated stability in water and acidic solutions compared to creatine monohydrate. Furthermore, creatine hydroxycitrates of the present invention may be useful to increase muscle and exercise performance in individual, athletes in particular, and to afford neuroprotective strategies addressing specific bioenergetic defects. In addition, by supplying biosignificant amounts of HCA, the creatine hydroxycitrates of the present invention may contribute to reduce fatty acid synthesis by preventing the conversion of carbohydrate energy into triglycerides, thereby being particularly suitable to be used in conjunction with dietary exercise regimens aimed at the reduction and/or prevention of excess adiposity leading to weight loss. Still further, the creatine hydroxycitrates of the present invention, due to the stimulatory action of the HCA moiety on serotonergic output, may contribute to improved exercise recovery and suppress the appetite of an individual, leading to weight loss.

Although the following examples illustrate the practice of the present invention in five of its embodiments, the examples should not be construed as limiting the scope of the invention. Other embodiments and modes of production will be apparent to those skilled in the art after consideration of the specification and the following examples.

EXAMPLES

Example 1

Creatine Dipotassium Hydroxycitrate Monohydrate, Dicreatine Monopotassium Hydroxycitrate Monohydrate, and Tricreatine Hydroxycitrate Monohydrate The fruits rinds of *G. cambogia* and *G. indica* may contain 20-30% (−)-HCA (Reference: Lewis, Y. S., and Neelakantan S. (−)-Hydroxycitric acids. The principle acid in the fruit *Garcinia cambogia. Pytochemistry* 4:619-625, 1965). To provide reaction yields of not less than 50% (−)-HCA on anhydrous basis acid content, the fruit rinds of *G. cambogia* and *G. indica* may preferably contain a minimum of about 15%(−)-HCA.

Accordingly, it is estimated that 208.13 g of (−)-HCA can be extracted from a starting amount of 1.3875 kg of Garcinia fruit rind. The extraction process may be similar to the process described by e.g. Majeed, M., et al. in U.S. Pat. No. 5,783,603, in which hydrosoluble (tri)potassium hydroxycitrate salts are described. That process involves the extraction of (−)-HCA from *Garcinia* fruit using an alkyl alcohol.

Step 1) 1.3875 kg of *Garcinia* fruit rind is extracted with 4.1625 l of methyl alcohol at about flux temperature for 3.5 hrs. the first extract is therefore collected following filtration with a cloth filter;

Step 2) An additional 4.1625 l of methyl alcohol is added to the *Garcinia* fruit rind and refluxed for 3.5 hrs. This is filtered as above to collect the second extract;

Step 3) An additional 4.1625 l of methyl alcohol is added again to the *Garcinia* fruit rind and refluxed for an additional 3.5 hrs. This is filtered as above to collect the third extract;

Step 4) All three are then combined;

Step 5) The combined extracts are treated with 4.1625 l of methyl alcohol to which 112.2 g of potassium hydroxide (2 mol elemental K) and 149.13 g creatine monohydrate (1 mol) are added at a pH between 9 and 10. This is again refluxed for 3.5 hrs. to attain a constant pH of 10 in order to precipitate (mono)-creatine dipotassium hydroxycitrate monohydrate;

Step 6) The precipitate is filtered and washed with 1.3875 l of methyl alcohol;

Step 7) The precipitate is dried under vacuum at about 70° C.

To obtain dicreatine (mono) potassium hydroxycitrate, the combined extracts in step 5 are treated with 4.1625 l of methyl alcohol to which 56.1 g of potassium hydroxide (1 mol elemental K) and 298.26 g creatine monohydrate (2 mol) are added at a ph of about 9-10. The is refluxed for 3.5 hrs. to attain constant pH of 10 in order to precipitate dicreatine (mono) potassium hydroxycitrate monohydrate. Steps 6 and 7 are repeated.

To obtain tricreatine hydroxycitrate, the combined extracts in step 5 are treated with 4.1625 l of methyl alcohol to which 447.39 g of creatine monohydrate (2 mol) are added at a ph of about 9-10. This is refluxed for 3.5 hrs. to attain a constant pH of 10 in order to precipitate tricreatine hydroxycitrate monohydrate. Steps 6 and 7 are repeated.

(Mono)-creatine dipotassium hydroxycitrate monohydrate preferably does not have less than 50% (−)-HCA and potassium and creatine content of about 20 and 10%, respectively, by weight on an anhydrous basis. The lactone content may be in the vicinity of not more than 2%.

Dicreatine (mono) potassium hydroxycitrate monohydrate preferably does not have less than 50% (−)-HCA and a potassium and creatine content of about 10 and 20%, respectively, by weight on an anhydrous basis. The lactone content may be in the vicinity of not more than 2%.

Tricreatine hydroxycitrate monohydrate preferable does not have less than 50% (−)-HCA and a creatine content of about 30% by weight on an anhydrous basis. The lactone content may be in the vicinity of not more than 2%.

(Mono)-creatine dipotassium hydroxycitrate monohydrate, Dicreatine (mono) potassium hydroxycitrate monohydrate and Tricreatine hydroxycitrate monohydrate are stable, hydrosoluble and bioavailable.

Example 2

Tricreatine Hydroxycitrate

Free (−)-HCA can easily be generated from calcium, sodium and potassium hydroxycitrate salts, by passing and aqueous solution of said salt through a cation exchange resin, e.g., Zeocarb® 225. (Reference: Singh, R. P., et al., (−)-Hydroxycitric acid from *Garcinia cambogia. Biological Memoirs* 21(1):27-33, 1995).

Hydroxycitric acid has a molecular weight of 208.13. Creatine monohydrate has a molecular weight of 149.13. Tricreatine hydroxycitrate may be manufactured as follows:

Step 1) Start with 10.84 l of anhydrous methyl alcohol;

Step 2) With stirring, an aqueous solution containing 1,084 g of hydroxycitric acid (5.2 moles), obtained after passing the (−)-HCA salt through a cation exchange resin, are added to the anhydrous methyl alcohol. The resulting mixture is stirred for approximately 45 minutes;

Step 3) 2,362 g (15.6 moles) or creatine monohydrate are added to the hydroxycitric acid/methyl alcohol mixture. This mixture is stirred for approximately four (4) hours;

Step 4) At the end of the four hours, the crystallized product is separated from the reaction mixture by centrifugation and washed with anhydrous methyl alcohol to remove all the impurities;

Step 5) the finished product is dried under vacuum at 70° C.

The resulting product is tricreatine hydroxycitrate, having three creatine cations per hydroxycitrate (tri)-anion. Creatine monohydrate has a molecular weight of 149.13; therefore the amount of creatine monohydrate added is 15.6 gram-moles.

Accordingly, given that the described reaction mixture includes 5.2 moles of hydroxycitric acid, the stoichiometric ratio of creatine to hydroxycitric acid is 3:1. The creatine assay for the material should be in the range of 60-70%.

Additionally, given that the reaction mixture includes 5.2 moles of hydroxycitric acid, by changing the stoichiometric ratio of creatine to hydroxycitrate to 1:1 and 2:1, monocreatine hydroxycitrate, and dicreatine hydroxycitrate, having one and two creatine cations per hydroxycitrate anion, respectively, can be obtained.

It should be noted that the preferred alcohols include methyl alcohol, ethyl alcohol, propyl and isopropyl alcohol. Also ethyl acetate (acetic acid ethyl ester) can be employed. Especially preferred is methyl alcohol. Hydroalcoholic solutions of (−)-HCA are preferred in order to reduce the conversion of creatine into creatinine during the time necessary for the reaction to be completed. Water (−)-HCA solutions could be alternatively used as media to which creatine monohydrate is added. The reaction however, would yield salts with lower creatine content.

Example 3

Preparation of Tricreatine Hydroxycitrate from Creatine Hydrochloride and (Tri)-Potassium Hydroxycitrate Monohydrate Tripotassium hydroxycitrate monohydrate has a molecular weight of 340.41 g per mole. Creatine hydrochloride has a theoretical molecular weight of 167.57 g per mole.

The procedure is a follows:

Step 1) 3.5 g of tripotassium hydroxycitrate monohydrate (0.01 mol) is mixed in sufficient deionized water to a final volume of 300 ml;

Step 2) To the solution described above, creatine hydrochloride is added in an amount of 5.03 g (0.03 mol) and solution is stirred for 45 minutes;

Step 3) The resulting product is tricreatine hydroxycitrate (5.8-6%), having three creatine cations per hydroxycitrate (tri)-anion.

Step 4) Potassium chloride, also obtains via this reaction, can be precipitated with the addition of alcohol (ethanol, methanol) and removed by filtration.

Given that the described reaction mixture includes 0.01 moles of tripotassium hydroxycitrate and 0.03 moles of creatine hydrochloride, the stoichiometric ratio of creatine to hydroxycitric acid is 3:1.

By changing the stoichiometric ration of creatine to hydroxycitric acid to 1:1 and 2:1, monocreatine dipotassium hydroxycitrate, and dicreatine monopotassium hydroxycitrate, having one and two creatine cation per hydroxycitrate anion respectively can be obtained. Accordingly, 0.01 and 0.02 mol of creatine hydrochloride respectively, per mol tripotassium hydroxycitrate can be utilized in step 2 of the reaction.

Example 4

Preparation of Tricreatine Hydroxycitrate from a Solution of Free (−)-HCA

Step 1) A solution is made by dissolving 1 mol (340.41 g) of tripotassium hydroxycitrate in a final volume of 2 l of deionized water to form an 0.5M solution;

Step 2) 1 mol of anhydrous citric acid (192.13 g) is added to the tripotassium hydroxycitrate solution in step 1. The solution is then heated at 30° C.;

Step 3) Upon cooling, tripotassium citrate precipitates. This is removed by filtration;

Step 4) A 10% solution of free (−)-HCA is obtained;

Step 5) 3 moles of creatine monohydrate (447.39 g) can then be obtained by adding 2 l of anhydrous methyl alcohol and then combined with the solution of free (−)-HCA. The mixture is stirred for 4 hrs. in order obtain tricreatine hydroxycitrate;

Step 6) At the end of the 4 hrs., the crystallized product is separated from the reaction mixture by centrifugation and washed with anhydrous methyl alcohol;

Step 7) The finished product is then dried under vacuum at 70° C. Dicreatine and monocreatine hydroxycitrate can be obtained by adding 2 or 1 mol of creatine monohydrate respectively to the mixture of anhydrous methyl alcohol and (−)-HCA, which is then stirred for 4 hrs.

Example 5

Production Method of Tricreatine Hydroxycitrate

Step 1) *Garcinia* rind is loaded into static extractors and extracted with water at a ratio between 5:1 and 7:1 for 60 minutes;

Step 2) The water is then drained to storage tank and 4 washes are preformed;

Step 3) The rind is discarded;

Step 4) A precipitation with calcium hydroxide is preformed and the calcium salt of hydroxycitric acid is recovered;

Step 5) The calcium hydroxycitric acid is treated with an acidic medium and filtered. Liquid hydroxycitric acid is recovered;

Step 6) Liquid hydroxycitric acid is reacted with creatine and then spray dried;

Step 7) Tricreatine HCA powder is recovered;

Step 8) The tricreatine HCA powder is sieved through a number 40 mesh, tested and packaged.

A typical yield via this process results in an HPLC assay of about 30-35% (−)-hydroxycitric acid and between 30 and 40% creatine.

The standard specification is for not less than 30% (−)-hydroxycitric acid and not less than 30% creatine. There should be not more than 8% of the product lost upon drying and not more than 10 ppm heavy metals. The product should be a fine powder with an "off-white" to "buff" colour.

The invention claimed is:

1. A supplemental dietary composition for oral use comprising creatine hydroxycitric acid in the form of a hydrosoluble salt of creatine and hydroxycitrate, wherein said composition is in the form of a capsule, tablet or a caplet.

2. The supplemental dietary composition of claim 1, wherein the salt has a molecular weight of 599.55.

3. The supplemental dietary composition of claim 1, wherein the salt has a melting point of about 290° C.

4. A method for at least one or promoting increased muscle and exercise performance and improving exercise recovery in individuals; the method including the step of consuming the supplemental dietary composition of claim 1.

5. The supplemental dietary composition of claim 1, wherein the composition additionally comprises one or more of the following dietary ingredients:

whey protein, casein, alpha lipoic acid, carbohydrates, free-form amino acids and salts, trivalent chromium and its organic salts and chelates, vitamins and minerals, *Camellia sinensis* leaf and its polyphenolic extracts, caffeine and other thermogenics, bioflavonoids, condensed tannins, oligomeric proanthocyanidins, American and/or Korean ginseng and their extracts, konjac glucomannan, creatinol, creatinol O-phosphate, creatinol sulfate, policosanol, and adaptogenic herbs and remedies.

6. The supplemental dietary composition of claim 5 comprising alpha lipoic acid.

7. The supplemental dietary composition of claim 5 comprising free-form amino acids and salts.

8. The supplemental dietary composition of claim 5 comprising trivalent chromium and its organic salts and chelates.

9. The supplemental dietary composition of claim 5 comprising vitamins and minerals.

10. The supplemental dietary composition of claim 5 comprising *Camellia sinensis* leaf and its polyphenolic extracts.

11. The supplemental dietary composition of claim 5 comprising caffeine and other thermogenics.

12. The supplemental dietary composition of claim 5 comprising bioflavonoids.

13. The supplemental dietary composition of claim 5 comprising American and/or Korean ginseng and their extracts.

14. The supplemental dietary composition of claim 5 comprising konjac glucomannan.

15. The supplemental dietary composition of claim 5 comprising creatinol.

16. The supplemental dietary composition of claim 5 comprising creatinol O-phosphate.

17. The supplemental dietary composition of claim 5 comprising creatinol sulfate.

18. The supplemental dietary composition of claim 5 comprising policosanol.

19. The supplemental dietary composition of claim 5 comprising adaptogenic herbs and remedies.

20. The supplemental dietary composition of claim 5 comprising alpha lipoic acid, free-form amino acids and salts, vitamins and minerals, caffeine and other thermogenics, and American and/or Korean ginseng and their extracts.

* * * * *